United States Patent

Piehler

(10) Patent No.: US 7,041,058 B2
(45) Date of Patent: May 9, 2006

(54) MEDICAL DIAGNOSTIC IMAGING SYSTEM AND METHOD FOR EFFICIENT ACCESS OF DATA

(75) Inventor: Michael J. Piehler, Renton, WA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 183 days.

(21) Appl. No.: 10/232,279

(22) Filed: Aug. 29, 2002

(65) Prior Publication Data

US 2004/0044666 A1    Mar. 4, 2004

(51) Int. Cl.
A61B 8/00 (2006.01)

(52) U.S. Cl. .................. 600/437; 600/444; 600/447; 600/459

(58) Field of Classification Search ........ 600/407–480; 369/13.01–44.42; 705/2–43
See application file for complete search history.

(56) References Cited

U.S. PATENT DOCUMENTS

| | | | |
|---|---|---|---|
| 5,715,823 A * | 2/1998 | Wood et al. ............... | 600/437 |
| 5,740,267 A * | 4/1998 | Echerer et al. ............ | 382/132 |
| 6,126,601 A * | 10/2000 | Gilling ....................... | 600/440 |
| 6,272,470 B1 * | 8/2001 | Teshima ..................... | 705/3 |
| 6,301,299 B1 * | 10/2001 | Sita et al. ................. | 375/240.01 |
| 6,468,213 B1 * | 10/2002 | Knell et al. ................ | 600/437 |
| 6,535,615 B1 * | 3/2003 | Zachmann et al. ........ | 382/100 |
| 6,547,730 B1 * | 4/2003 | Lin et al. ................... | 600/437 |
| 6,574,629 B1 * | 6/2003 | Cooke, Jr. et al. ........ | 707/10 |
| 6,595,921 B1 * | 7/2003 | Urbano et al. ............. | 600/437 |
| 2002/0082948 A1 * | 6/2002 | Panelli ....................... | 705/27 |
| 2003/0000535 A1 * | 1/2003 | Galloway et al. .......... | 128/896 |

OTHER PUBLICATIONS searchDatabase.com Definitions, "CORBA" http://searchdatabase.techtarget.com/sDefinition/0,,sid13_gci213865,00.html, 2 pages (Feb. 25, 2001).

searchDatabase.com Definitions, "dynamic link library" http://searchdatabase.techtarget.com/sDefinition/0,,sid13_gci213902,00.html, 1 page (Jul. 26, 2001).

searchDatabase.com Definitions, "compiler" http://searchdatabase.techtarget.com/sDefinition/0,,sid13_gci211824,00.html, 1 page (Dec. 6, 2000).

* cited by examiner

Primary Examiner—Eleni Mantis-Mercader
Assistant Examiner—William Jung

(57) ABSTRACT

The preferred embodiments described herein provide a medical diagnostic imaging system and method for efficient access of data. In one preferred embodiment, a medical diagnostic imaging system is provided comprising a software application, a text file, and a software component that binds to the software application at runtime. The text file and the software component store common data. If the medical diagnostic imaging system is being used in a first mode of operation (e.g., during the manufacturing process at the factory), data is read from the text file. If the medical diagnostic imaging system is being used in a second mode of operation (e.g., during normal workflow of the ultrasound system in the field), data is read from the software component. These preferred embodiments can be used to provide fast access to stored data during the manufacturing process without incurring performance penalties. Other preferred embodiments are provided, and each of the preferred embodiments described herein can be used alone or in combination with one another.

24 Claims, 2 Drawing Sheets

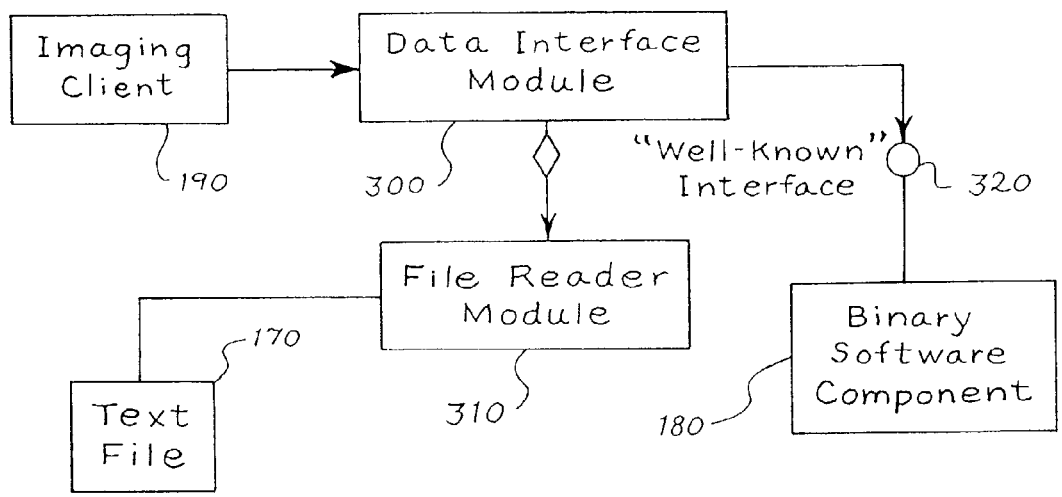
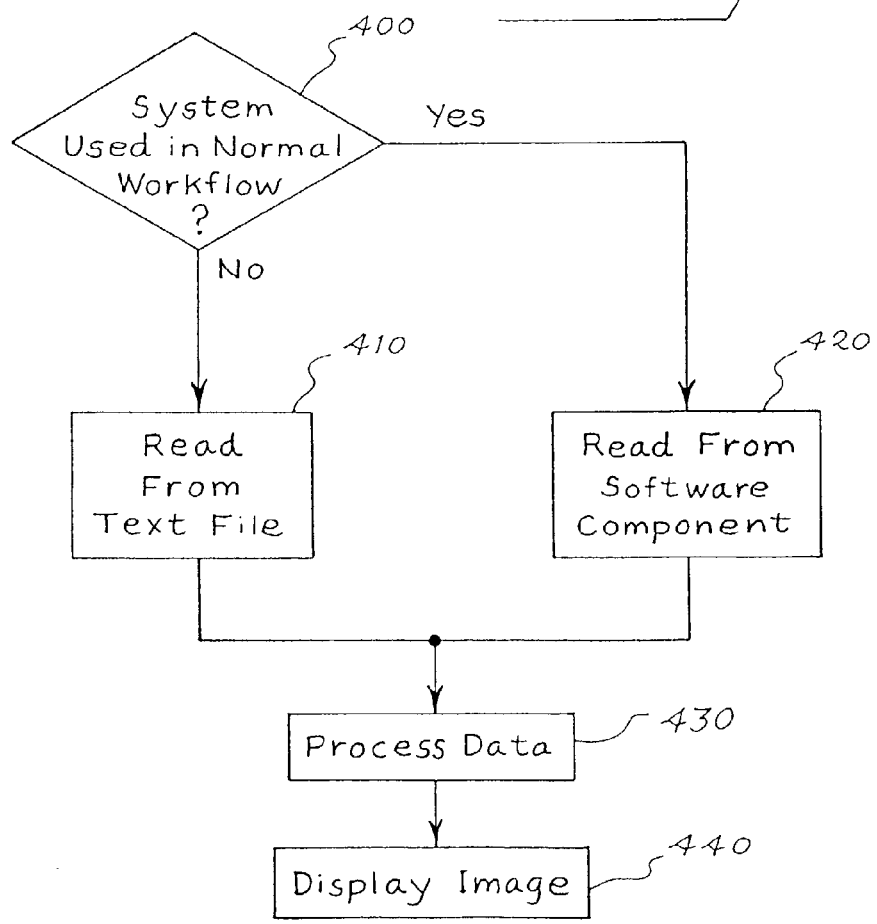

MEDICAL DIAGNOSTIC IMAGING SYSTEM AND METHOD FOR EFFICIENT ACCESS OF DATA

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

REFERENCE TO COMPUTER PROGRAM LISTING APPENDIX

This application contains one compact disc submitted in duplicate. The material on that compact disc is hereby incorporated by reference. The following is a listing of the names of the files on the compact disc, their dates of creation, and their sizes in bytes.

Directory of BinStream\Source:

| Date | Time | Size | Name |
|---|---|---|---|
| 05/16/2002 | 04:16 p | 557 | CspMap.cpp |
| 05/16/2002 | 04:16 p | 2,935 | CspMapImpl.cpp |
| 05/16/2002 | 04:16 p | 1,208 | CspNameTagMap.cpp |
| 05/16/2002 | 04:16 p | 10,628 | CspNameTagMapImpl.cpp |
| 05/16/2002 | 04:16 p | 756 | Directory.cpp |
| 05/16/2002 | 04:17 p | 7,445 | DirectoryImpl.cpp |
| 05/16/2002 | 04:17 p | 2,685 | Field.cpp |
| 05/16/2002 | 04:17 p | 8,257 | FieldAbs.cpp |
| 05/16/2002 | 04:17 p | 2,760 | FieldFactory.cpp |
| 05/16/2002 | 04:17 p | 4,196 | FieldServer.cpp |
| 05/16/2002 | 04:18 p | 2,557 | IndexAbs.cpp |
| 05/16/2002 | 04:18 p | 331 | IndexFactoryAbs.cpp |
| 05/16/2002 | 04:18 p | 1,018 | Makefile |
| 05/16/2002 | 04:18 p | 750 | NameAbs.cpp |
| 05/16/2002 | 04:18 p | 2,193 | Record.cpp |
| 05/16/2002 | 04:18 p | 17,940 | RecordImpl.cpp |
| 05/16/2002 | 04:18 p | 1,570 | SchemaParser.cpp |
| 05/16/2002 | 04:18 p | 7,146 | SchemaParserImpl.cpp |
| 05/16/2002 | 04:19 p | 3,593 | Store.cpp |
| 05/16/2002 | 04:19 p | 415 | StoreMgr.cpp |
| 05/16/2002 | 04:19 p | 1,093 | StreamAbs.cpp |

Directory of BinStream\Source\Include:

| Date | Time | Size | Name |
|---|---|---|---|
| 05/16/2002 | 04:17 p | 2,431 | DirectoryImpl.h |
| 05/16/2002 | 04:17 p | 5,384 | RecordImpl.h |
| 05/16/2002 | 04:18 p | 656 | StoreMgr.h |
| 05/16/2002 | 04:17 p | 1,644 | DomUtils.h |
| 05/16/2002 | 04:17 p | 1,050 | CspMapImpl.h |
| 05/16/2002 | 04:18 p | 2,466 | SchemaParserImpl.h |
| 05/16/2002 | 04:17 p | 3,424 | CspNameTagMapImpl.h |

Directory of BinStream\Include:

| Date | Time | Size | Name |
|---|---|---|---|
| 05/16/2002 | 04:13 p | 674 | DataTypes.h |
| 05/16/2002 | 04:14 p | 8,795 | Field.h |
| 05/16/2002 | 04:14 p | 5,119 | FieldAbs.h |
| 05/16/2002 | 04:14 p | 969 | FieldFactory.h |
| 05/16/2002 | 04:14 p | 1,575 | FieldName.h |
| 05/16/2002 | 04:15 p | 1,017 | NameAbs.h |
| 05/16/2002 | 04:15 p | 2,826 | Record.h |
| 05/16/2002 | 04:15 p | 1,541 | Store.h |
| 05/16/2002 | 04:15 p | 2,049 | StreamAbs.h |
| 05/16/2002 | 04:14 p | 2,369 | IndexAbs.h |
| 05/16/2002 | 04:14 p | 767 | IndexFactoryAbs.h |
| 05/16/2002 | 04:14 p | 1,467 | Directory.h |
| 05/16/2002 | 04:15 p | 644 | StoreAbs.h |
| 05/16/2002 | 04:13 p | 954 | CspMap.h |
| 05/16/2002 | 04:14 p | 609 | MultiCast.h |
| 05/16/2002 | 04:15 p | 1,769 | ReadBinaryFile.h |
| 05/16/2002 | 04:15 p | 1,818 | SchemaParser.h |
| 05/16/2002 | 04:13 p | 1,549 | CspNameTagMap.h |

Directory of BinStream\Include\Interfaces:

| Date | Time | Size | Name |
|---|---|---|---|
| 09/09/2000 | 03:37 p | 4,410 | BoolField.h |
| 09/09/2000 | 03:36 p | 422 | BoolField.idl |
| 09/09/2000 | 03:36 p | 908 | BoolField_i.c |
| 09/09/2000 | 03:37 p | 12,791 | BoolField_p.c |
| 06/09/2000 | 04:47 p | 4,465 | DoubleField.h |
| 06/09/2000 | 04:47 p | 423 | DoubleField.idl |
| 06/09/2000 | 04:47 p | 912 | DoubleField_i.c |
| 06/09/2000 | 04:46 p | 12,850 | DoubleField_p.c |
| 05/16/2002 | 04:14 p | 793 | FieldServer.h |
| 06/09/2000 | 04:47 p | 4,433 | FloatField.h |
| 06/09/2000 | 04:47 p | 418 | FloatField.idl |
| 06/09/2000 | 04:47 p | 910 | FloatField_i.c |
| 06/09/2000 | 04:47 p | 12,813 | FloatField_p.c |
| 06/09/2000 | 04:47 p | 4,369 | IntField.h |
| 06/09/2000 | 04:48 p | 408 | IntField.idl |
| 06/09/2000 | 04:48 p | 906 | IntField_i.c |
| 06/09/2000 | 04:48 p | 12,742 | IntField_p.c |
| 09/09/2000 | 03:37 p | 1,501 | InterfaceTypes.h |
| 06/09/2000 | 04:48 p | 4,401 | LongField.h |
| 06/09/2000 | 04:48 p | 413 | LongField.idl |
| 06/09/2000 | 04:48 p | 908 | LongField_i.c |
| 06/09/2000 | 04:48 p | 12,777 | LongField_p.c |
| 06/09/2000 | 04:49 p | 3,984 | Record.h |
| 06/09/2000 | 04:49 p | 336 | Record.idl |
| 06/09/2000 | 04:49 p | 902 | Record_i.c |
| 06/09/2000 | 04:50 p | 9,708 | Record_p.c |
| 06/09/2000 | 04:48 p | 4,433 | ShortField.h |
| 06/09/2000 | 04:48 p | 418 | ShortField.idl |
| 06/09/2000 | 04:48 p | 910 | ShortField_i.c |
| 06/09/2000 | 04:48 p | 12,814 | ShortField_p.c |
| 06/09/2000 | 04:48 p | 4,459 | StringField.h |
| 06/09/2000 | 04:48 p | 417 | StringField.idl |
| 06/09/2000 | 04:48 p | 912 | StringField_i.c |
| 06/09/2000 | 04:48 p | 13,421 | StringField_p.c |
| 06/09/2000 | 04:49 p | 4,425 | UintField.h |
| 06/09/2000 | 04:49 p | 437 | UintField.idl |
| 06/09/2000 | 04:49 p | 908 | UintField_i.c |
| 06/09/2000 | 04:49 p | 12,809 | UintField_p.c |
| 06/09/2000 | 04:49 p | 4,457 | UlongField.h |
| 06/09/2000 | 04:49 p | 442 | UlongField.idl |
| 06/09/2000 | 04:49 p | 910 | UlongField_i.c |
| 06/09/2000 | 04:49 p | 12,844 | UlongField_p.c |
| 06/09/2000 | 04:49 p | 4,489 | UshortField.h |
| 06/09/2000 | 04:49 p | 447 | UshortField.idl |
| 06/09/2000 | 04:49 p | 912 | UshortField_i.c |
| 06/09/2000 | 04:49 p | 12,881 | UshortField_p.c |
| 12/07/2000 | 03:23 p | 1,523 | dlldata.c |
| 05/16/2002 | 04:14 p | 2,178 | PtrHash.h |

Directory of BinStream\Util:

| Date | Time | Size | Name |
|---|---|---|---|
| 10/17/2001 | 04:09 p | 28,939 | XmlToDll.pl |
| 10/17/2001 | 04:09 p | 4,271 | MakeGen.pl |
| 05/17/2002 | 10:57 a | 11,026 | RecGen.pl |

BACKGROUND

Medical diagnostic imaging systems often store read-only data that is accessed during the normal workflow of the system. For example, ultrasound imaging systems can store imaging performance data sets in text files on a hard disk. By storing the data in a text file, the manufacturer can effectively "tune" the data without having to write and re-write software. However, because these data sets are quite large, runtime performance becomes sluggish due to inefficiencies in reading data from the hard disk. To combat this, the data can be cached during system start-up so that the data is accessed from random access memory, which is much more efficient than disk access. This approach moves the performance penalty from the user's normal workflow to system start-up. However, lengthening start-up time is often not acceptable, especially in portable systems.

There is a need, therefore, for a medical diagnostic imaging system and method for efficient access of data.

SUMMARY

The present invention is defined by the following claims, and nothing in this section should be taken as a limitation on those claims.

By way of introduction, the preferred embodiments described below provide a medical diagnostic imaging system and method for efficient access of data. In one preferred embodiment, a medical diagnostic imaging system is provided comprising a software application, a text file, and a software component that binds to the software application at runtime. The text file and the software component store common data. If the medical diagnostic imaging system is being used in a first mode of operation (e.g., during the manufacturing process at the factory), data is read from the text file. If the medical diagnostic imaging system is being used in a second mode of operation (e.g., during normal workflow of the ultrasound system in the field), data is read from the software component. These preferred embodiments can be used to provide fast access to stored data during the manufacturing process without incurring performance penalties. Other preferred embodiments are provided, and each of the preferred embodiments described herein can be used alone or in combination with one another.

The preferred embodiments will now be described with reference to the attached drawings.

BRIEF DESCRIPTION OF THE DRAWINGS

FIG. 3 is a block diagram of a software structure of a preferred embodiment.

FIG. 4 is a flow chart of a method for reading imaging performance data of a preferred embodiment.

DETAILED DESCRIPTION OF THE PRESENTLY PREFERRED EMBODIMENTS

Figure 1:
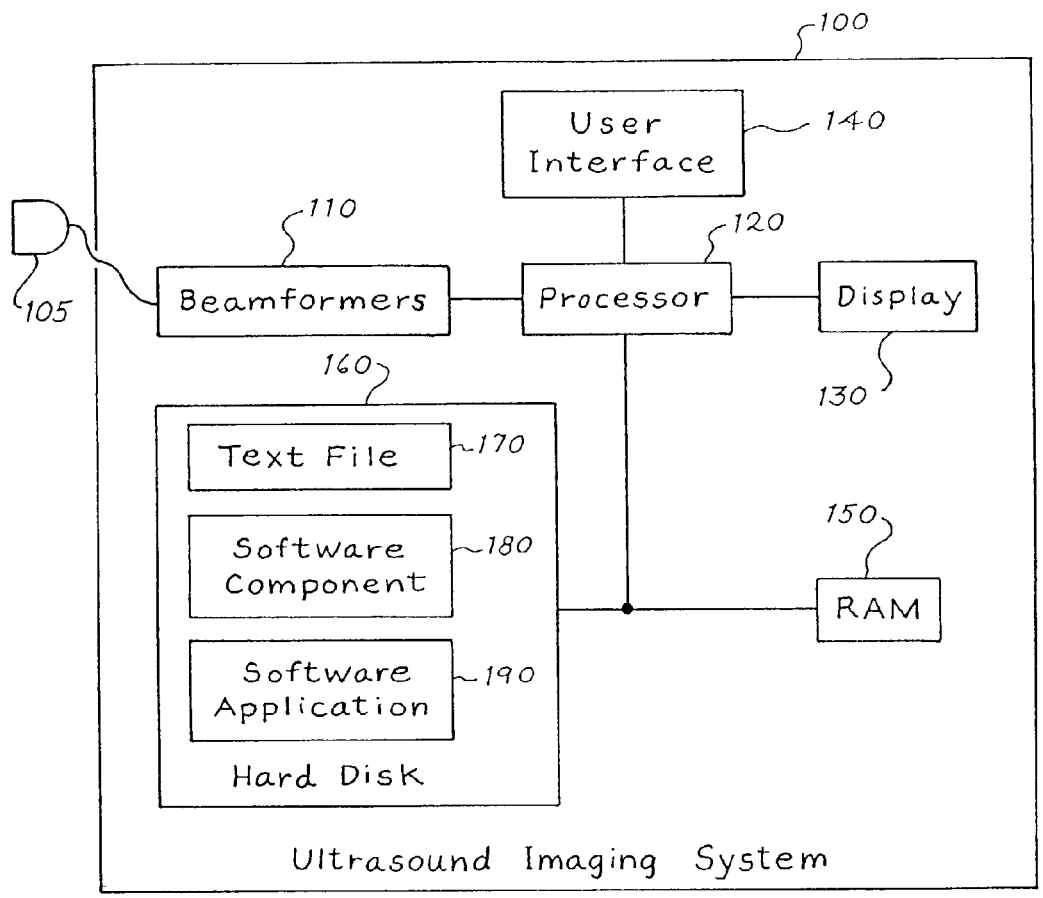
FIG. 1 is a block diagram of a medical diagnostic ultrasound imaging system of a preferred embodiment.

Turning now to the drawings, FIG. 1 is a block diagram of a medical diagnostic ultrasound imaging system 100 of a preferred embodiment. While an ultrasound system is used to illustrate this preferred embodiment, it should be noted that other types of medical imaging acquisition systems can be used. In this preferred embodiment, the ultrasound system 100 comprises a transducer (or "probe") 105, transmit and receive beamformers 110, a processor 120, a display device 130, a user interface 140, random access memory (RAM) 150, and a hard disk 160, which stores a text file 170, a software component 180, and a software application 190. (The software application 190 will sometimes be referred to herein as "operational software," an "imaging client," or "ultrasound system software.") The ultrasound system 100 can comprise other components, which are not shown in FIG. 1 for simplicity. Additionally, while a hard disk 160 is used in this preferred embodiment, it should be noted that other types of storage devices, such as a solid-state memory device, can be used for data storage and that multiple storage devices can be used (e.g., two hard disks).

When the ultrasound system 100 is turned on, the software application 190 is loaded in the ultrasound system's RAM 150 during system start-up and is executed by the processor 120. As used herein, the term "software application" refers to computer-readable program code that is executed by the processor 120 to control the various hardware and software components of the ultrasound system 100 to create an ultrasound image. During an ultrasound examination, the software application 190 causes the beamformers 110 to apply a voltage to the transducer 105 to cause it to vibrate and emit an ultrasonic beam into a portion of a patient's body in contact with the transducer 105. Ultrasonic energy reflected from the patient's body impinges on the transducer 105, and the resulting voltages created by the transducer 105 are received by the beamformers 110. The software application 190 processes the sensed voltages to create an ultrasound image and displays the image on the display device 130. The software application 190 can also provide additional functionality, such as, but not limited to, report generation and measurement tools.

The text file 170 stored on the hard disk 160 contains data that the software application 190 uses for image optimization. For example, the text file 170 can include imaging performance data sets (or "optimization parameters") for each of a plurality of transducers. Imaging performance data sets can contain values for one or more of the following parameters: transmit power, dynamic range, electromagnetic characteristics, field-of-view shape, frame rate, geometry of probe, filter, and gain. In operation, the software application 190 identifies the type of transducer 105 being used, and the associated optimization parameters are used by the software application 190 to produce an optimized ultrasound image. The text file 170 can also contain other data in addition to imaging performance data sets, such as system configuration information (e.g., maximum number of transmit elements and focal zones) and video performance information (e.g., color maps). Further optimization can be based on the type of exam (e.g., obstetrics, cardiology, etc.). Data in the text file 170 is preferably read-only.

Imaging performance data sets and other data are stored in a text file 170 on the hard disk 160 to provide an ultrasound engineer (or "image optimizer") at the factory with fast access to the stored data. Generating imaging performance data sets for transducers at the factory is an iterative process. The ultrasound engineer repeatedly changes values in a data set and observes the resulting changes in a generated image until the image is optimized. Generating imaging performance data sets is a time-consuming process, which sometimes requires making hundreds of changes to the text file 170. By storing imaging performance data sets in a text file 170, the ultrasound engineer can quickly and effectively "tune" the data during the manufacturing process without having to write and re-write software. In one preferred embodiment, the imaging performance data sets stored in the text file 170 are formatted in extensible Markup Language (XML). This format is easily parsed and displayed with web browsers, and a host of parsers is readily available that simplifies loading the data from the text file 170.

While using a text file 170 provides ultrasound engineers with fast access to the stored data, runtime performance of the imaging system 100 can become sluggish due to the large amount of data in the text file 170 and the inefficiencies in reading data from the hard disk 160. To combat this, the data in the text file 170 can be cached during system start-up so that the data is accessed from RAM 150, which is accessed much more efficiently than the hard disk 160. This approach moves the performance penalty from the user's normal workflow to system start-up. However, lengthening start-up time is often not acceptable, especially in portable systems. To achieve both efficient workflow and faster start times, it is preferred to avoid disk access as much as possible. To achieve this end, the image optimizer at the manufacturer can "hard-code" the performance data in a compiled language (such as C++), compile that source code, and effectively have read-only memory. However, this approach requires that the image optimizer be software savvy, which is not always the case.

In this preferred embodiment, a "best of both worlds" approach is provided that provides ultrasound engineers with fast access to the stored data during the manufacturing process without incurring performance penalties and without requiring the ultrasound engineer to be software savvy. Under this approach, data is stored on the hard disk 160 as both a text file 170 and as a software component 180. The software component 180 preferably comprises a dynamic-link library (DLL) that is bound to the software application 190 at run time. The data is accessed from the text file 170 during a first mode of operation (e.g., during the manufacturing process at the factory), and the data is accessed using the software component 180 during second mode of operation (e.g., during normal workflow of the ultrasound system 100 in the field). Before turning to the operational details of this preferred embodiment, the software application 190 and the software component 180 are discussed.

As mentioned above, the software application 190 is computer-readable program code executed by the processor 120 to control the various hardware and software components of the ultrasound system 100 to create an ultrasound image. The software application 190 is created by the manufacturer of the ultrasound system 100 as source code and is compiled into a plurality of binary object code files. The binary object code files are linked together to form a monolithic, executable program. At some point, identifiers in the program (such as a function name, constant, subroutine label, or variable) are assigned a meaning, and symbolic addresses in the program are converted to storage-related addresses. This process is known as binding and can occur during compilation (compile-time binding), during linking (link-time binding), or at the time the program is executed (run-time binding). In this preferred embodiment, binding of the software application 190 occurs during compilation or linking. Binding at these states is referred to as static or early binding.

The software component 190 is an individual modular software routine that is built independent from the software application 190 and is dynamically linked to the software application 190. By being dynamically linked to the software application 190, the software component 180 binds to the software application 190 during runtime (i.e., during the execution of the software application 190) rather than when the software application 190 is compiled or linked. Binding at this stage is referred to as run-time, late, or dynamic binding. A distributed technology, such as Microsoft's Component Object Model (COM) or Common Object Request Broker Architecture (CORBA), can be used to achieve runtime binding. In this preferred embodiment, the software component 180 is structured as an object conforming to the COM architecture.

Because the software component 180 is bound with the software application 190 at run-time rather than when the software application 190 is compiled or linked, an ultrasound engineer can tune the imaging performance data in parallel with a software designer building the software application 190. Because the software application 190 is a stand-alone program that is complete without the binary software component, the designer of the software application 190 does not need to have knowledge of the imaging performance data sets when building the software application 190. Further, the software application 190 does not need to be changed if there are changes made to the software component 180.

Figure 2:
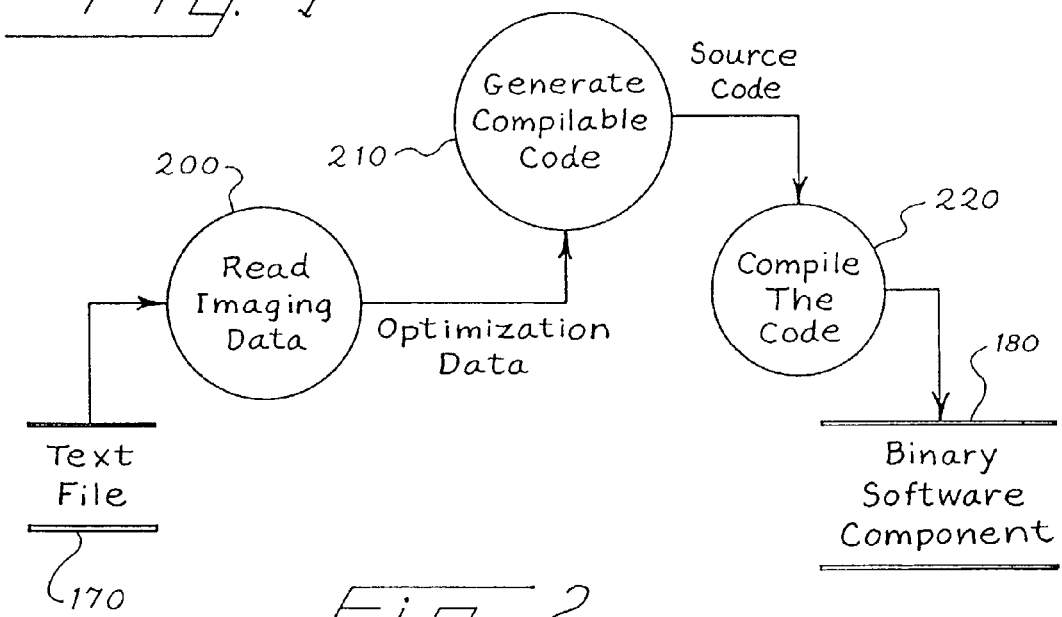
FIG. 2 is a flow chart of a method for generating binary software components of a preferred embodiment.

In order to ensure that the software component 180 and the text file 170 share the exact same representation, the source code for the software component 180 is preferably automatically generated from the text file 170 during the manufacturing process in parallel to the software application 190 being built. This process is shown in the flow chart of FIG. 2. In this method, a tool parses the imaging data from the text file, which can contain other data in addition to the imaging performance data sets, such as system configuration information and video performance information (act 200). Next, compilable source code is generated from the image optimization data (act 210), and the source code is compiled into the binary software component 180 (act 220). In the preferred embodiment, a Practical Extraction and Report Language (Perl) script is used to convert the XML text file 170 to C++ components.

Turning again to the drawings, FIG. 3 is a block diagram of a software structure that will be used to illustrate the operation of this preferred embodiment. In FIG. 3, the software application 190 is referred to as the imaging client. The imaging client 190 is in communication with a data interface module 300, which communicates with a file reader module 310 (to read data from the text file 170) and with a well-known interface 300 (to read data from the binary software component 180). FIG. 4 is a flow chart of a method for runtime access of imaging optimization data and will be used to illustrate the operation of the software structure depicted in FIG. 3.

Because imaging performance data is stored both in the text file 170 and in the software component 180 in the ultrasound system 100, a decision needs to be made as to which item should be accessed to read the data. In this preferred embodiment, the imaging client 190 has no notion of where the data is coming from and gets the data through the data interface module 300, which is responsible for deciding where the data is coming from. In operation, when the imaging client 190 request the data, the data interface module 300 determines whether the ultrasound system is being used in normal workflow (act 400). As used herein, "normal workflow" occurs when the ultrasound system 100 is used in the field (i.e., after the ultrasound system 100 leaves the factory). The ultrasound system 100 is not used in "normal workflow" when optimization parameters are being tuned at the factory. The data interface module 300 checks a software switch, which is turned on by the user prior to starting the software application 190, to see if the ultrasound system 100 is or is not being used in a normal workflow. In this preferred embodiment, the decision as to whether the ultrasound system 100 is being used in normal workflow is made at runtime via an environment variable, registry entry, or some other similar mechanism.

If the ultrasound system 100 is not being used in normal workflow, the data interface module 300 asks the file reader module 310 to load the data (using the well-known interface 320) from the text file 170 when the software application 190 requests the data. The file reader module 310 is preferably an XML file reader. While loading data from a text file has undesirable performance characteristics and is not very efficient, it is tolerable because the desired end is optimizing image quality. Further, by accessing data from a text file, ultrasound image optimization engineers do not have to climb a steep learning curve to understand the text file, which is easily manipulated during their optimization efforts at the factory. Additionally, cycle time is very short between changing the file content and seeing the results on the imaging system. Rapid prototyping is facilitated by the shortened cycle time. After the data is read from the text file 170, the data is processed (act 430), and an image is displayed (act 440).

If the ultrasound system 100 is being used in normal workflow, such as when an end user is conducting an ultrasound examination of a patient, the data interface module 300 explicitly links to the binary software component 180 when the software application 190 requests the data. When the ultrasound system 100 is used in the field, optimum performance is desired, and if the data were accessed from the text file 170 during normal workflow, workflow performance could be negatively impacted. By pre-processing read-only data from the text file 170 into the software component 180, both start-up and runtime performance of the ultrasound system 100 is improved. When the ultrasound system 100 is used in the field, the software switch tells the system 100 that it is operating in a normal workflow. The data is then loaded from the software component 180, which is an exact binary representation of the text file 170 used during image optimization in the factory, instead of the text file 170. By reading the performance data from the compiled, binary software component 180 when the ultrasound system 100 is used in the field, the negative impact to performance characteristics is avoided.

In summary, these preferred embodiments enable high performance access to factory-defined read-only data for medical diagnostic medical imaging platforms. By storing data in a text file and in a software component, the data is both easily accessible by ultrasound engineers at the factory and quickly accessible when the ultrasound system is used in normal workflow. It should be noted that while the data in the preferred embodiments described above took the form of imaging performance data, other data can be used, such as, but not limited to, system configuration information, preset information, and video performance information. Accordingly, a specific type of data set (e.g., an imaging performance data set) should not be read into the claims unless explicitly recited therein. Further, the specific software languages used above should not be read into the claims. It should also be noted that while the data read from the text file 170 and the software component 180 was read only data in the embodiments described above, appropriate modifications can be made to implement these preferred embodiments with write-many data.

Finally, as noted above, although an ultrasound imaging system was used to illustrate these preferred embodiments, other types of medical image acquisition systems can be used. For example, a medical image acquisition device that uses any of the following imaging modalities can be used: computed tomography (CT), magnetic resonance imaging (MRI), computed radiography, magnetic resonance, angioscopy, color flow Doppler, cystoscopy, diaphanography, echocardiography, fluoresosin angiography, laparoscopy, magnetic resonance angiography, positron emission tomography, single-photon emission computed tomography, x-ray angiography, computed tomography, nuclear medicine, biomagnetic imaging, culposcopy, duplex Doppler, digital microscopy, endoscopy, fundoscopy, laser surface scan, magnetic resonance spectroscopy, radiographic imaging, thermography, and radio fluroscopy. Other types of imaging modalities can be used, and the claims should not be limited to a specific type of imaging modality or medical image acquisition system unless explicitly recited therein.

The CD-ROM appendix contains a computer program listing for a presently preferred embodiment. The specific embodiment disclosed in that appendix should not be read as a limitation on the following claims.

It is intended that the foregoing detailed description be understood as an illustration of selected forms that the invention can take and not as a definition of the invention. It is only the following claims, including all equivalents, that are intended to define the scope of this invention.

What is claimed is:

1. A method for accessing data in a medical diagnostic imaging system, the method comprising a computer readable medium:
   (a) providing a medical diagnostic imaging system comprising a software application, a text file, and a software component that binds to the software application at runtime, wherein the text file and the software component store common data, and wherein the text file comprises data selected from the group consisting of imaging performance data sets for a transducer, transmit power, dynamic range, electromagnetic characteristics, field-of-view shape, frame rate, geometry of probe, filter, gain, system configuration information, maximum number of transmit elements, maximum number of focal zones, video performance information, and color maps;
   (b) determining whether the medical diagnostic imaging system is being used in a first mode of operation or a second mode of operation;
   (c) if the medical diagnostic imaging system is being used in the first mode of operation, reading data from the text file; and
   (d) if the medical diagnostic imaging system is being used in the second mode of operation, reading data from the software component.

2. The invention of claim 1, wherein the first mode of operation occurs at a factory.

3. The invention of claim 1, wherein the second mode of operation occurs in the field.

4. The invention of claim 1, wherein (b) comprises determining whether the medical diagnostic imaging system is being used in the first mode of operation or the second mode of operation by analyzing an environment variable.

5. The invention of claim 1, wherein (b) comprises determining whether the medical diagnostic imaging system is being used in the first mode of operation or the second mode of operation by analyzing a registry entry.

6. The invention of claim 1 further comprising generating the software component from the text file.

7. The invention of claim 1, wherein the text file is formatted in extensible Markup Language (XML).

8. The invention of claim 1, wherein the software component comprises a Dynamically Linked Library (DLL).

9. The invention of claim 1, wherein the data comprises imaging performance data.

10. The invention of claim 1, wherein the medical diagnostic imaging system comprises an ultrasound imaging system.

11. A medical diagnostic imaging system comprising:
a software application;
a text file, wherein the text file comprises data selected from the group consisting of imaging performance data sets for a transducer, transmit power, dynamic range, electromagnetic characteristics, field-of-view shape, frame rate, geometry of probe, filter, gain, system configuration information, maximum number of transmit elements, maximum number of focal zones, video performance information, and color maps; and
a software component that binds to the software application at runtime, wherein the text file and the software component store common data;
wherein, during a first mode of operation of the medical diagnostic ultrasound imaging system, data is read from the text file; and wherein, during a second mode of operation of the medical diagnostic imaging system, data is read from the software component.

12. The invention of claim 11, wherein the first mode of operation occurs at a factory.

13. The invention of claim 11, wherein the second mode of operation occurs in the field.

14. The invention of claim 11, wherein the text file is formatted in extensible Markup Language (XML).

15. The invention of claim 11, wherein the software component comprises a Dynamically Linked Library (DLL).

16. The invention of claim 11, wherein the data comprises imaging performance data.

17. The invention of claim 11, wherein the medical diagnostic imaging system comprises an ultrasound imaging system.

18. The invention of claim 11 further comprising:
a data interface module in communication with the software application; and
a file reader module in communication with the data interface module.

19. A method for accessing read-only data in a medical diagnostic imaging system, the method comprising a computer readable medium:
(a) providing a medical diagnostic imaging system comprising a software application, a text file, and a software component that binds to the software application at runtime, wherein the text file and the software component store common read-only data, and wherein the text file comprises data selected from the group consisting of imaging performance data sets for a transducer, transmit power, dynamic range, electromagnetic characteristics, field-of-view shape, frame rate, geometry of probe, filter, gain, system configuration information, maximum number of transmit elements, maximum number of focal zones, video performance information, and color maps;
(b) determining whether the medical diagnostic imaging system is being used in a first mode of operation or a second mode of operation;
(c) if the medical diagnostic imaging system is being used in the first mode of operation, reading read-only data from the text file; and
(d) if the medical diagnostic imaging system is being used in the second mode of operation, reading read-only data from the software component.

20. A medical diagnostic imaging system comprising:
a software application;
a text file, wherein the text file comprises data selected from the group consisting of imaging performance data sets for a transducer, transmit power, dynamic range, electromagnetic characteristics, field-of-view shape, frame rate, geometry of probe, filter, gain, system configuration information, maximum number of transmit elements, maximum number of focal zones, video performance information, and color maps; and
a software component that binds to the software application at runtime, wherein the text file and the software component store common read-only data;
wherein, during a first mode of operation of the medical diagnostic imaging system, read-only data is read from the text file; and wherein, during a second mode of operation of the medical diagnostic imaging system, read-only data is read from the software component.

21. A method for accessing data in a medical diagnostic imaging system, the method comprising a computer readable medium:
(a) altering data in a text file of a medical diagnostic imaging system;
(b) creating a software component from the text file, whereby the software component and the text file store common data;
(c) executing a software application of the medical diagnostic imaging system;
(d) binding the software component to the software application; and
(e) accessing the data stored in the software component;
wherein the text file comprises data selected from the group consisting of imaging performance data sets for a transducer, transmit power, dynamic range, electromagnetic characteristics, field-of-view shape, frame rate, geometry of probe, filter, gain, system configuration information, maximum number of transmit elements, maximum number of focal zones, video performance information, and color maps.

22. The invention of claim 21, wherein (a)–(b) are performed prior to an end user receiving the medical diagnostic imaging system, and wherein (c)–(e) are performed after the end user receives the medical diagnostic imaging system.

23. The invention of claim 21, wherein the data comprises imaging performance data.

24. The invention of claim 21, wherein the medical diagnostic imaging system comprises an ultrasound imaging system.

* * * * *